United States Patent [19]
Peled

[11] Patent Number: 4,898,900
[45] Date of Patent: Feb. 6, 1990

[54] 3,3-OXY-BIS{[2,2'-DI(BROMOMETHYL)]} PROPANOIC ACID DERIVATIVES

[75] Inventor: Michael Peled, Beer-Sheva, Israel

[73] Assignee: Bromine Compounds Ltd., Beer-Sheva, Israel

[21] Appl. No.: 290,154

[22] Filed: Dec. 27, 1988

[30] Foreign Application Priority Data

Dec. 28, 1987 [IL] Israel .......................... 84953

[51] Int. Cl.$^4$ .............. C07C 103/727; C07C 103/147; C07C 59/315; C07C 69/708; C08K 5/20; C08K 5/11; C08K 5/09

[52] U.S. Cl. ..................... 524/220; 524/288; 524/307; 524/319; 560/180; 562/583; 564/158; 564/159

[58] Field of Search .............. 524/220, 288, 307, 366, 524/377, 380, 319; 560/180; 562/583; 564/155, 159, 158; 568/676, 680, 844

[56] References Cited

U.S. PATENT DOCUMENTS

| | | | |
|---|---|---|---|
| 3,196,175 | 7/1965 | Wakasa et al. | 568/844 |
| 3,607,953 | 9/1971 | Hurley | 568/676 |
| 3,700,625 | 10/1972 | Brady et al. | 524/366 |
| 3,864,306 | 2/1975 | Dieckmann | 524/288 |
| 3,872,155 | 3/1975 | Dieckmann | 524/288 |
| 4,001,182 | 1/1977 | Murtha et al. | 524/288 |
| 4,725,638 | 2/1988 | Ellmann et al. | 524/412 |

Primary Examiner—Veronica P. Hoke
Attorney, Agent, or Firm—Michael N. Meller

[57] ABSTRACT

Novel derivatives of 3,3'-oxy-bis{[2,2'-di(bromomethyl)]propanoic acid} of formula (1)

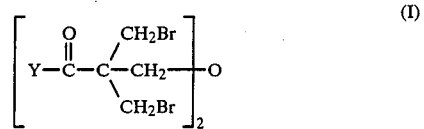

in which Y represents OR, chlorine or NH—R and wherein R represents hydrogen or an alkyl, aralkyl or aryl group, in which the alkyl, aryl and aralkyl groups are unsubstituted or substituted with 1 to 5 bromine atoms, are described.

The novel derivatives of the invention have improved thermal properties and a high content of bromine, and are particularly suitable as flame-retardant agents. Methods of preparation of these novel compounds are described.

17 Claims, No Drawings

3,3-OXY-BIS{[2,2'-DI(BROMOMETHYL)]} PROPANOIC ACID DERIVATIVES

FIELD OF THE INVENTION

The present invention relates to novel derivatives of 3,3'-oxy-bis([2,2'di(bromomethyl)]propanoic acid), to process for their preparation and their use as flame-retardant agents.

BACKGROUND OF THE INVENTION 3,3'-Oxy-bis([2,2'-di(bromomethyl)]propanoic acid), referred to hereinafter as "diacid" for the sake of brevity, has the formula:

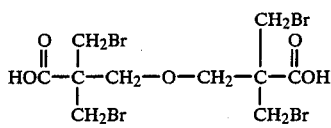

The diacid is, in turn, a derivative of the well-know flame-retardant compound Didinol, which is employed to obtain V-2 polypropylene (according to UL94 standard), and which has the formula:

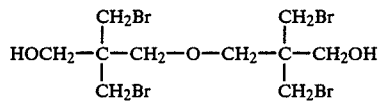

The art is constantly seeking for flame-retardant agents which present high thermal stability as well as high melting points. The thermal properties of the flame-retardant compounds are of paramount importance in the preparation of flame-retardant compositions and articles which incorporate them, because of the relatively high temperatures that these compounds are required to withstand during processing of plastics. On the other hand, health and evironmental requirements make it preferable to provide compounds which are free from the danger of liberating dioxines or benzofurans.

SUMMARY OF THE INVENTION

It has now been found, and this is an object of the invention, that novel derivatives of the diacid can be prepared, which possess improved thermal properties, both from the point of view of melting point and of thermal stability, and whose bromine content is relatively high, thereby making them suitable flame-retardant agents.

It has further been found, and this is another object of the invention, that several derivatives can be conveniently prepared starting from the diacid of didinol, through relatively simple processes.

DETAILED DESCRIPTION OF THE INVENTION

The novel compounds according to the invention have the general formula (I)

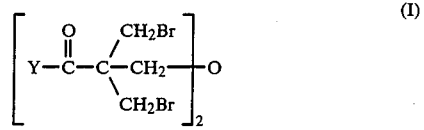

in which Y represents OR, chlorine or NH—R and wherein R represents hydrogen or an alkyl, aralkyl or aryl group, wherein the alkyl, aryl and aralkyl groups are unsubstituted or substituted with 1 to 5 bromine atoms.

Examples of preferred compounds of the invention are those in which R is phenyl or anilino, each unsubstituted or substituted with 1 to 5 bromine atoms, or tribromopentaerithrityl.

Specific examples of compounds of the invention are:
3,3'-Oxy-bis{[2,2'-di(bromomethyl)]propanoic acid};
3,3'-Oxy-bis{[2,2'-di(bromomethyl)]propanoyl chloride};
3,3'-Oxy-bis{[2,2'-di(bromomethyl)]propanamide};
3,3'-Oxy-bis{N-2,4,6-tribromophenyl[2,2'-di(bromomethyl)]propanamide} (BET);
3,3'-Oxy-bis{2,4,6-tribromophenyl[2,2'-di(bromomethyl)]propionate};
3,3'-Oxy-bis{2,4,6-tribromophenyl[2,2'-di(bromomethyl)]propionate};
3,3'-Oxy-bis{tribromopentaerithrityl[2,2'-di(bromomethyl)propionate]} (BETR); and
3,3'-Oxy-bis{pentabromobenzyl[2,2'-di(bromomethyl)]propionate}.

The invention is also directed to flame-retardant compositions comprising a synthetic resin and a compound according to the invention, alone or in admixture with flame-retardant synergisitic materials and/or additives. Synthetic resins to which it is possible to impart flame-retardant properties are, inter alia, polyester resins, polypropylene and acrylonitrile-butadiene-styrene.

Such compounds have been found to possess excellent thermal stability as well as high melting points, and are adapted to be used as flame-retardant additives in a variety of synthetic resins, such as polyesters, polypropylene and acrylonitrile-butadiene-styrene resins (ABS).

The heat stability of the compounds of the invention is illustrated in Table I, which shows the Thermal Gravimetric Analysis (TGA) of some compounds according to the invention, as compared to comparable derivatives of tribromopivalic acid. The compounds of the invention show, in all cases, a thermal stability higher by about 50° C. than that of the corresponding derivatives of pivalic acid. The compounds listed in Table I are identified by their chemical formula in Table II.

TABLE I

| Compound | M.P. (°C.) | TGA (10° C./min under air) % weight loss at given temperature °C. | | | |
|---|---|---|---|---|---|
| | | 1% | 2% | 5% | 10% |
| di-OH | 188–190 | 226 | 235 | 247 | 255 |
| TBP | 101–103 | 217 | 238 | 266 | 290 |
| di-TBP(BET) | 157–159 | 297 | 310 | 325 | 335 |
| Trinol | 92–93 | 192 | 208 | 240 | 263 |
| di-Trinol(BETR) | 124–125 | 265 | 295 | 320 | 330 |
| Pentabromo benzyl | 151–153 | 246 | 265 | 295 | 315 |
| di-Pentabromo | 205–206 | 280 | 300 | 315 | 323 |

TABLE I-continued

| Compound | M.P. (°C.) | TGA (10° C./min under air) % weight loss at given temperature °C. | | | |
|---|---|---|---|---|---|
| | | 1% | 2% | 5% | 10% |
| benzyl | | | | | |

TABLE II

| | Compound Identification | |
|---|---|---|
| Compound Name | R for compounds of Formula (CH$_2$Br)$_3$CCO$_2$R | R for compounds of Formula O—[—CH$_2$(CH$_2$Br)$_2$CCO$_2$R]$_2$ |
| di-OH | | H |
| TBP | φBr$_3$ | |
| di-TBP(BET) | | φBr$_3$ |
| Trinol | (CH$_2$Br)$_3$CCH$_2$— | |
| di-Trinol (BETR) | | (CH$_2$Br)$_3$CCH$_2$— |
| Pentabromobenzyl | —CH$_2$—φBr$_5$ | |
| di-Pentabromobenzyl | | —CH$_2$—φBr$_5$ |

EXAMPLE 1

3,3′-Oxy-bis{[2,2′-di(bromomethyl)]propanoic acid}

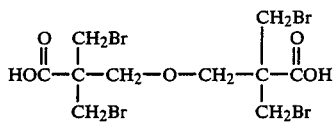

To a three-necked 2-liter flask equipped with a condenser and a mechanical stirrer there were added 840 ml (13.3 moles) of nitric acid, which was then heated to 95° C. 300 gr (0.59 moles) of didinol were then added in small portions during 2 hours. A precipitate appeared during this addition step. After addition was completed stirring was continued at 95° C. for an additional 3 hours after which period the reaction mixture was cooled to room temperature, one liter of water was added and the mixture was filtered. The filter cake was washed with water in order to remove traces of acid, and was then dried at 60° C. under vacuum to a constant weight. 274 gr of the diacid of didinol were obtained in 87% yield, m.p. 189°–193° C. The following characterizing data were obtained: % bromine: clcd. 59.9; found 59.3. NMR (acetone d$_6$): 3.73(S, CH$_2$Br), 3.82(S,CH$_2$O). Purity: 0.2270 gr of the product were titrated with 8.128 ml NaOH solution 0.1N, corresponding to a 99.1% purity of the diacid. IR (KBr): 1700 cm$^{-1}$.

EXAMPLE 2

3,3′-Oxy-bis{[2,2′-di(bromomethyl)]propanoyl chloride)}

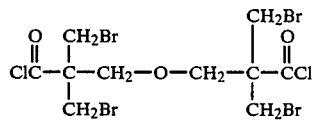

To a 550 ml three-necked flask equipped with a mechanical stirrer, a condenser and a CaCl$_2$ drying tube there were added 100 g (0.19 moles) of the diacid obtained in Example 1, and 180 ml (1.49 moles) of thionyl chloride. The reaction mixture was heated to reflux and maintained under reflux conditions for about 6 hours, until no more HCl evolved, after which time the excess thionyl chloride was evaporated under vacuum. The product was crystallized from acetonitrile and 95 g of product were obtained, corresponding to a 90% yield with respect to the diacid. m.p. 91°–92° C.; NMR (CDCl$_3$): 3.70 (8H, S), 3.92 (4H, S).

EXAMPLE 3

3,3′-Oxy-bis{[2,2′-di(bromomethyl)]propanamide}

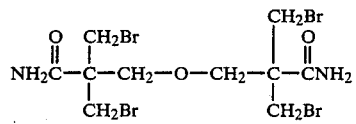

To a 100 ml three-necked flask there were added 10 g of the dichloride obtained in Example 2 and 50 ml of a concentrated (28%) aqueous ammonia solution. The reaction mixture was stirred at room temperature for 12 hours and the product crystallized during this period. The precipitate was filtered, washed with water and dried in a vacuum oven to constant weight. The final weight of the product was 5.7 g (61% yield based on the dichloride). m.p. 136°–138° C.; % bromine: clcd.: 60.1, found: 60.2; NMR(δCDCl$_3$): 3.7 (8H, d of d), 3.9 (S, 4H).

EXAMPLE 4

3,3′-Oxy-bis{N-2,4,6-tribromophenyl[2,2′-di(bromomethyl)]propanamide} (BET)

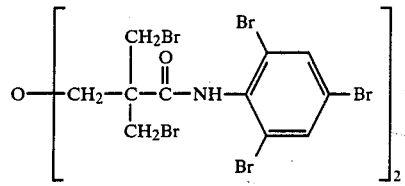

To a 50 ml three-necked flask equipped with a stirrer there were added 14 g tribromoaniline and 11.5 g of the dichloride obtained in Example 2. This solid mixture was heated to and kept at 145° C. during 12 hours, after which period the mixture was cooled to room temperature, the aqueous layer was taken away, and 50 cc of toluene and 1 gr of activated carbon were added. The mixture was then filtered and the product was recrystallized twice from toluene. 8.2 g of the product were obtained corresponding to a 36% yield relative to the dichloride. m.p. 196°–197° C.; IR: 1680, 1630 cm$^{-1}$; NMR (CDCl$_3$); 3.84 (8H, AB), 4.23 (S, 4H), 7.72 (4H, S).

EXAMPLE 5

3,3'-Oxy-bis{2,4,6-tribromophenyl[2,2'-di(bromomethyl)]propionate}

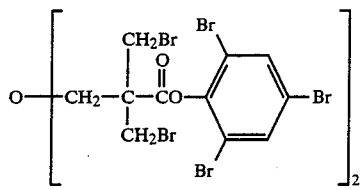

To a 500 ml three-necked flask equipped with a mechanical stirrer and a condenser there were added 300 ml of acetonitrile, 11.4 g (0.02 moles) of the dichloride obtained in Example 2, 15.6 g (0.04 moles) of tribromophenol and 5 g of $Na_2CO_3$ dissolved in 7 ml of water. The mixture was stirred during 12 hours at 50° C., after which period the product was filtered and cyrstallized from Tetrahydrofuran and petrol ether 60-80. 9.7 g of product were obtained with a 40% yield respective to the dichloride. m.p. 157-159; %bromine: clcd.: 69.0, found: 69.0; NMR (CDCL$_3$): 3.94 (S, 8H), 4.11 (S, 4H), 7.72 (S, 4H). IR (KBr): 1780 cm$^{-1}$.

EXAMPLE 6

3,3'-Oxy-bis{tribromopentaerithrityl[2,2'-di(bromomethyl) propionate]} (BETR)

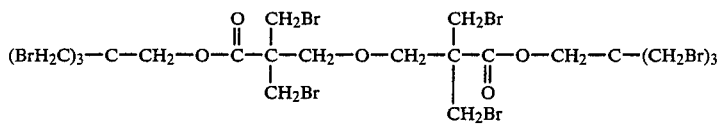

To a 100 ml three-necked flask equipped with a stirrer and a condenser there were added 11.4 ml (0.02 moles) of the dichloride obtained in Example 2 and 13 g (0.04 moles) of tribromopentaerithritol (3-bromo-2,2'-di(-bromomethyl)propanol). The solid mixture was heated to melting (about 100° C.) and kept at that temperature during about 6 hours, until no more HCl evolved. After this period 50 ml toluene and activated carbon were added to the mixture. The resulting mixture was filtered and the solvent evaporated. The product was crystallized from dichloromethane and petrol ether 60-80. m.p. 124°-125° C.; %bromine: clcd.: 69.7, found: 69.7; NMR (CDCl$_3$): 3.56 (12H, S), 3.65 (8H, S) 3.80 (4H, S), 4.33 (4H, S).

EXAMPLE 7

3,3'-Oxy-bis{pentabromobenzyl[2,2'-di(bromomethyl)]-propionate}

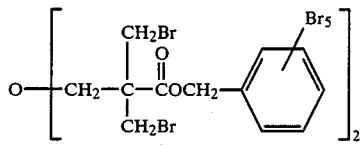

To a 100 ml three-necked flask equipped with a stirrer there were added 15.6 g (0.23 moles) of pentabromobenzyl alcohol and 5.7 g (0.01 moles) of the dichloride obtained in Example 2. The mixture was heated to 175° C. and kept at this temperature during 5 hours. The reaction mixture was cooled to room temperature, dissolved in dichloromethane and washed with an alkaline aqueous solution (pH~10). The product was isolated by chromatography and recrystallized from chloroform. m.p. 205°-206° C. NMR (CDCl$_3$): 3.63 (8H, S), 3.77 (4H, S), 5.65 (4H, S).

The following examples illustrate the use of the compounds of the invention as flame-retardant additives for synthetic resins. The data reported in the examples were obtained according to the following standard tests:

Flammability: UL-94 vertical burning test in a flammability hood (according to Underwrites Laboratories, Inc.); UL-588 burning test in a flammability hood (according to Underwrites Laboratories, Inc., Jan. 14, 1986); and Limiting oxygen index (LOI) (ASTM D 2863-77) on a FTA Flammability Unit Stanton Redcroft.

Izod notched impact energy: (ASTM D 256-81) on a Pendulum impact tester type 5102 Zwick.

HDT: Deflection temperature under felxural load (18.5 kg/cm$^2$) (ASTM D 648-72) on a CEAST 6055.

U.V. Stability: Accelerated weathering test-irradiation for 250 hrs and measuring of the color change by color deviation, on an Accelerated Weathering Tester Q-U-V (B-lamps), (The Q-Panel Co.).

Color Deviation: (DE) Color measurement and comparison with reference specimen, on a Spectro Color Meter SCM-90, (TechnoInstruments Ltd.), after accelerated weathering test.

EXAMPLE 8

Three flame-retarded polypropylene formulations were prepared, employing three different FR compounds: a compound of the invention (BET-bis ester tribromophenol, prepared according to Example 5), a compound known as FR-930 (ex Akzo), and a compound known as BN-451 (Saytex BN-451, ex Ethyl Corporation). The three formulas were tested in the UL-94 and UL-588 burning tests. The results of these tests are set forth in Table III, which also details the components of each formulation. From the data of Table III it can be seen that all FR compounds provide the same flame-retardancy grade. All percentages given are in weight percent.

TABLE III

| Components | Formulation | | |
|---|---|---|---|
| | I | II | III |
| Polypropylene, % | 91.6 | 91.5 | 91.5 |
| FR employed | BET | FR-930 | BN-451 |
| % FR | 5.8 | 5.5 | 5.5 |
| Antimony trioxide, % | 2.4 | 2.8 | 2.8 |
| Irganox B225*, % | 0.2 | 0.3 | 0.3 |
| Bromine, % | 4.0 | 3.7 | 2.5 |
| UL-94 Test: | | | |
| Total Flaming Time, sec. | 25 | 9 | 10 |
| Maximal Flaming Time, sec. | 7 | 3 | 4 |
| Number of Dripping Specimens Igniting Cotton | 5 | 5 | 5 |
| Class: | V2 | V2 | V2 |
| UL-588 Test: | | | |

TABLE III-continued

| Components | Formulation | | |
|---|---|---|---|
| | I | II | III |
| Class | pass | pass | pass |

*UV stabilizer (ex Ciba-Geigy AG)

EXAMPLE 9

Three ABS compositions, each comprising a different flame-retardant material, were tested in order to evaluate the UV stability thereof. The first composition contained a compound of the invention (BETR-bis ester of Trinol prepared according to Example 6), the second contained octabromodiphenylether (Octa-ex Bromine Compounds Ltd.), and the third contained the compound commercially known as FF-680 (ex Ethyl Corporation). The results for these specimens are detailed in Table IV, from which it can be seen that BET has a UV stability comparable to that of FF-680, and superior to that of Octa.

TABLE IV

| Components | Formulation | | |
|---|---|---|---|
| | I' | II' | III' |
| ABS, % | 74.8 | 76.8 | 74.9 |
| FR employed | BET | Octa | FF-680 |
| % FR | 20.1 | 18.1 | 20.0 |
| Antimony trioxide, % | 5.1 | 5.1 | 5.1 |
| Bromine, % | 14 | 14 | 14 |
| UL-94, 1.6 mm | VO | VO | VO |
| Izod Notched Impact, J/m | 76.4 | 113 | 49 |
| DE-at time 0 hrs | 31.3 | 32 | 30 |
| DE-at time 250 hrs | 46 | 57 | 47 |

The above description and examples have been given for the purpose of illustration and are not intended to be limitative. Many variations can be effected in the processes of the invention, and many different derivatives according to the invention can be prepared, without exceeding the scope of the invention.

I claim:

1. 3,3'-Oxy-bis{[2,2'-di(bromomethyl)]propanoic acid} derivatives of formula (I)

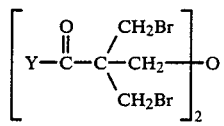

in which Y represents OR, chlorine or NH—R and wherein R represents hydrogen or an alkyl, aralkyl or aryl group, wherein the alkyl, aryl and aralkyl groups are unsubstituted or substituted with 1 to 5 bromine atoms.

2. A compound according to claim 1, wherein R is phenyl, unsubstituted or substituted with 1 to 5 bromine atoms.

3. A compound according to claim 1, wherein R is anilino, unsubstituted or substituted by 1 to 5 bromine atoms.

4. A compound according to clain 1, wherein R is tribromopentaerithrityl.

5. 3,3'-Oxy-bis{[2,2'-di(bromomethyl)]propanoic acid}.

6. 3,3'-Oxy-bis{[2,2'-di(bromomethyl)]propanoyl chloride}.

7. 3,3'-Oxy-bis{[2,2'-di(bromomethyl)]propanamide}.

8. 3,3'-Oxy-bis{N-2,4,6-tribromophenyl[2,2'-di(bromomethyl)]propanamide}.

9. 3,3'-Oxy-bis{2,4,6-tribromophenyl[2,2'-di(bromomethyl)]propionate}.

10. 3,3'-Oxy-bis{tribromopentaerithritol[2,2'-di(bromomethyl)propionate]}.

11. 3,3'-Oxy-bis{pentabromobenzyl[2,2'-di(bromomethyl)]propionate}.

12. A flame-retardant composition comprising a synthetic resin and a compound of Formula I according to claim 1, alone or in admixture with conventional flame-retardant synergistic materials additives or mixtures thereof.

13. A flame-retardant composition according to claim 12, wherein the synthetic resin is selected from the group consisting of polyesters, polypropylene and acrylonitrile-butadiene-styrene.

14. A flame retardant composition comprising a synthetic resin and a compound of formula I of claim 1, wherein R is substituted or unsubstituted phenyl or anilino, wherein said substituents are 1 to 5 bromine atoms or R is tribromopentaerithrityl; alone or in admixture with conventional flame retardant synergistic materials.

15. A flame retardant composition according to claim 12 wherein the compound of formula I is selected from the group consisting of
3,3'-Oxy-bis-{[2,2'-di(bromomethyl)]propanoic acid},
3,3'-Oxy-bis{[2,2'-di(bromomethyl)]propanoyl chloride},
3,3'-Oxy-bis{[2,2'-di(bromomethyl)]propanamide},
3,3'-Oxy-bis{N-2,4,6-tribromophenyl[2,2'-di(bromomethyl)]propanamide},
3,3'-Oxy-bis{2,4,6-tribromophenyl[2,2'-di(bromomethyl)]propionate},
3,3'-Oxy-bis{tribromopentaerithrityl[2,2'-di(bromomethyl)propionate]}, and
3,3'-Oxy-bis(pentabromobenzyl[2,2'-di(bromomethyl)]propionate).

16. A flame-retardant composition according to claim 14, wherein the synthetic resin is selected from the group consisting of polyesters, polypropylene and acrylonitrile-butadiene-styrene.

17. A flame-retardant composition according to claim 15, wherein the synthetic resin is selected from the group consisting of polyesters, polypropylene and acrylonitrile-butadiene-styrene.

* * * * *